(12) United States Patent
Hoffman

(10) Patent No.: US 6,473,486 B2
(45) Date of Patent: Oct. 29, 2002

(54) SYSTEM AND METHOD OF COMPUTED TOMOGRAPHY IMAGING USING A FOCUSED SCINTILLATOR AND METHOD OF MANUFACTURING

(75) Inventor: David M. Hoffman, New Berlin, WI (US)

(73) Assignee: GE Medical Systems Global Technology Co., LLC, Waukesha, WI (US)

( * ) Notice: Subject to any disclaimer, the term of this patent is extended or adjusted under 35 U.S.C. 154(b) by 0 days.

(21) Appl. No.: 09/681,048

(22) Filed: Dec. 5, 2000

(65) Prior Publication Data

US 2002/0067796 A1 Jun. 6, 2002

(51) Int. Cl.[7] .................................................. G01T 1/20
(52) U.S. Cl. .......................................... 378/19; 250/367
(58) Field of Search ............................ 378/19, 98.8, 4, 378/15; 250/367, 366

(56) References Cited

U.S. PATENT DOCUMENTS

| | | | | |
|---|---|---|---|---|
| 4,234,792 A | * | 11/1980 | DeCou et al. | 250/361 R |
| 4,291,228 A | * | 9/1981 | Thompson | 250/363 S |
| 4,560,882 A | * | 12/1985 | Barbaric et al. | 250/487.1 |
| 4,700,074 A | * | 10/1987 | Bonjakovic | 250/363 S |
| 4,855,589 A | * | 8/1989 | Enck et al. | 250/213 |
| 5,091,650 A | * | 2/1992 | Uchida et al. | 250/366 |
| 5,241,180 A | | 8/1993 | Ishaque et al. | |
| 5,519,227 A | * | 5/1996 | Karellas | 250/483.1 |
| 6,061,419 A | | 5/2000 | Hsieh et al. | 378/4 |
| 6,091,840 A | | 7/2000 | Hu et al. | 382/131 |
| 6,115,448 A | | 9/2000 | Hoffman | 378/19 |
| 6,118,839 A | | 9/2000 | Dafio et al. | 378/15 |
| 6,252,927 B1 | * | 6/2001 | Weiczorek | 378/19 |
| 6,304,626 B1 | * | 10/2001 | Adachi et al. | 378/19 |

* cited by examiner

Primary Examiner—Robert H. Kim
Assistant Examiner—Irakli Kiknadze
(74) Attorney, Agent, or Firm—Timothy J. Ziolkowski; Michael A. Della Penna; Carl B. Horton

(57) ABSTRACT

The present invention provides a detector for a CT imaging system. The detector includes a focused scintillator for receiving and converting high frequency electromagnetic energy to light energy. The detector further includes a photodiode positioned adjacent to the scintillator and configured to receive light energy discharged through a light exiting surface of the scintillator. The detector also includes electrical leads to transmit signals from the photodiode to a data processing unit for image construction. The CT system also provides for a gantry having an output for projecting high frequency electromagnetic energy toward the scintillator. A method of use and method of fabricating the tapered scintillators of the tapered scintillator array are also disclosed.

15 Claims, 4 Drawing Sheets

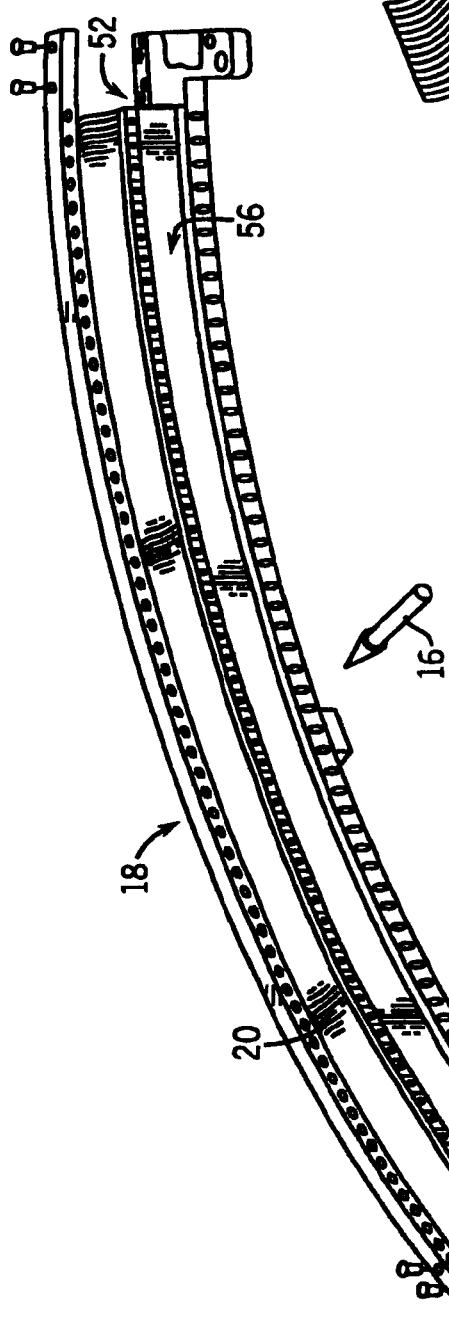
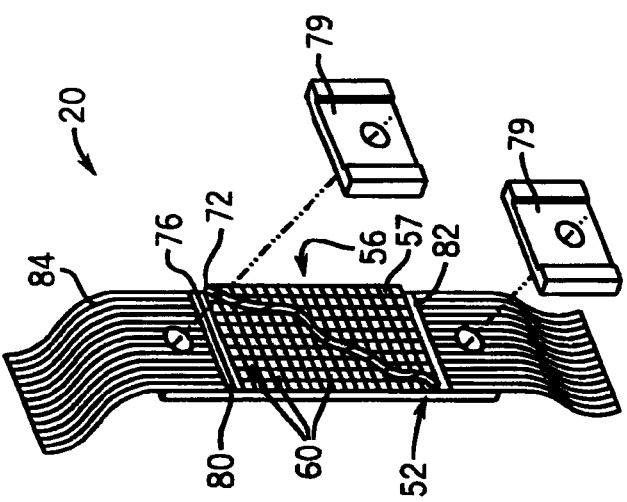
FIG. 3
FIG. 4

SYSTEM AND METHOD OF COMPUTED TOMOGRAPHY IMAGING USING A FOCUSED SCINTILLATOR AND METHOD OF MANUFACTURING

BACKGROUND OF INVENTION present invention relates generally to computed tomography imaging and, more particularly, to an apparatus and method of converging light energy for use with computed tomography systems.

Typically in computed tomography (CT) imaging systems, an x-ray source emits a fan-shaped beam toward an object, such as a patient. The beam, after being attenuated by the object, impinges upon an array of radiation detectors. The intensity of the attenuated beam radiation received at the detector array is typically dependent upon the attenuation of the x-ray beam by the object. Each detector element of the detector array produces a separate electrical signal indicative of the attenuated beam received by each detector element. The-electrical signals are transmitted to a data processing unit for analysis which ultimately results in the formation of an image.

Generally, the x-ray source and the detector array are rotated with a gantry within an imaging plane and around the object. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator.

Typically, each scintillator of a scintillator array has an x-ray entrance area dimensionally equivalent to a light exiting area. As a result, to effectively receive the light energy exiting the scintillator, it is necessary for each photodiode adjacent thereto to have a light receiving area dimensionally similar to the light exiting area of the scintillator. While it is possible to implement a photodiode having a light receiving area smaller than the light existing area of the scintillator, it is certainly not desirable as significant portions of the light energy exiting the scintillator would not be detected by the photodiode. Because a photodiode array having therein a plurality of photodiodes is typically formed on a silicon chip, significant surface area to accommodate the photodiodes is necessary. Reducing the size of the light exiting surface of each scintillator would therefore result in a smaller total active area for each of the photodiodes. Hence, more open or unused portions between active areas of the chip could be available for other purposes.

It would therefore be desirable to have a focused scintillator capable of receiving high frequency electromagnetic energy and converging light energy to a light exiting surface.

SUMMARY OF INVENTION

The present invention provides a detector for a CT imaging system. The detector includes a focused scintillator for receiving and converting high frequency electromagnetic energy to light energy. The detector further includes a photodiode positioned adjacent to the scintillator and is configured to receive light energy discharged through a light exiting surface of the scintillator. The detector also includes electrical leads connected from the photodiode to a data processing unit. Signal outputs of the photodiodes are transmitted to the data processing unit to facilitate image reconstruction. The CT system provides for a gantry having an output for projecting high frequency electromagnetic energy toward the tapered scintillator. All of which overcome the aforementioned drawbacks.

In accordance with one aspect of the invention, a computed tomography system is provided. The system includes a tapered scintillator array having at least one tapered scintillator therein capable of receiving high frequency electromagnetic energy. The system also includes an output positioned in a gantry for projecting the high frequency electromagnetic energy toward the tapered scintillator array. At least one photodiode forming a photodiode array is optically coupled to the tapered scintillator array for receiving light energy therefrom.

In accordance with another aspect of the invention, a scintillator for a CT system is provided. The scintillator includes an entrance surface defined by a plurality of entrance edges configured to receive high frequency energy. A plurality of walls extend directionally to a plurality of exiting edges configured concentric to the plurality of entrance edges and are configured to converge light energy. The scintillator also includes an exiting surface defined by the plurality of exiting edges configured to discharge the light energy.

The invention also includes a method-of imaging for a CT system. The method includes projecting high frequency electromagnetic energy to a tapered scintillator array formed by a plurality of tapered scintillators. The method further includes converting high frequency electromagnetic energy to light energy and then converging the light energy to a photodiode array formed by a plurality of photodiodes.

Another aspect of the present invention is to provide a method to produce high density detectors for a CT system. The method includes providing a plurality of tapered scintillators forming a tapered scintillator array configured to receive high frequency electromagnetic energy. The method also includes providing a plurality of photodiodes forming a photodiode array optically connected to the tapered scintillator array and configured to receive light energy discharged from the tapered scintillator array. The method also includes connecting a plurality of leads to the photodiode array capable of transmitting electrical outputs of the photodiode array.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention. In the drawings:

FIG. 3 is a perspective view of a CT system detector array.

FIG. 4 is a perspective view of a detector shown in FIG. 3.

DETAILED DESCRIPTION

The operating environment of the present invention is described with respect to a four-slice computed tomography (CT) system. However, it will be appreciated by those of ordinary skill in the art that the present invention is equally applicable for use with single-slice or other multi-slice configurations. Moreover, the present invention will be described with respect to the detection and conversion of x-rays. However, one of ordinary skill in the art will further appreciate, that the present invention is equally applicable for the detection, conversion, and convergence of other high frequency electromagnetic energy.

Figure 1:
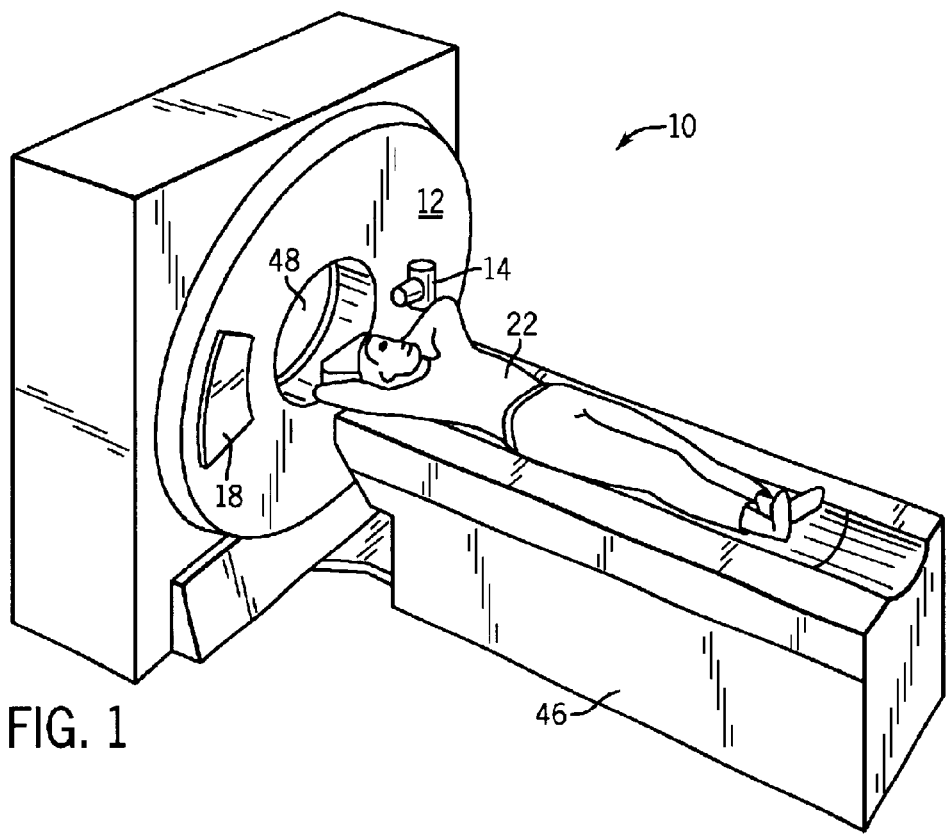
FIG. 1 is a pictorial view of a CT imaging system.
Figure 2:
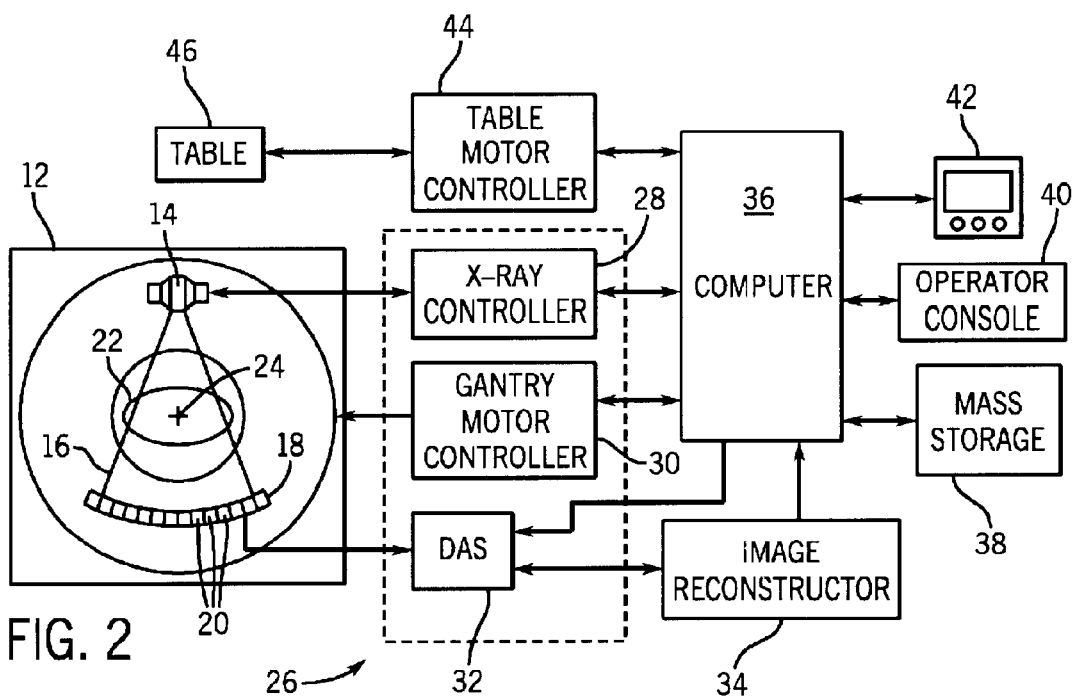
FIG. 2 is a b lock schematic diagram of the system illustrated in FIG. 1.

Referring to FIGS. 1 and 2, a computed tomography (CT) imaging system 10 is shown as including a gantry 12 representative of a third generation CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

As shown in FIGS. 3 and 4, detector array 18 includes a plurality of detectors 20. Each detector 20 includes a high density photodiode array 52 and a multi-dimensional scintillator array 56 positioned above the photodiode array 52. A collimator (not shown) is positioned above the scintillator array 56 to collimate x-ray beams 16 before such beams impinge upon scintillator array 56. Photodiode array 52 includes a plurality of photodiodes 60, deposited or formed on a silicon chip. Scintillator array 56, as known in the art, is positioned over the photodiode array 52. Photodiodes 60 are optically coupled to scintillator array 56 and are capable of transmitting signals representative of the light output of the scintillator array 56. Each photodiode 60 produces a separate low level analog output signal that is a measurement of the attenuated beam entering a corresponding scintillator 57 of scintillator array 56. Photodiode output lines 76 may, for example, be physically located on one side of detector 20 or on a plurality of sides of detector 20. As shown in FIG. 4, photodiode output lines 76 are located on opposing sides of the photodiode array 52.

In one embodiment, as shown in FIG. 3, detector array 18 includes 57 detectors 20. Each detector 20 includes a photodiode array 52 and scintillator array 56, each having an array size of 16×16. As a result, arrays 52 and 56 have 16 rows and 912 columns (16×57 detectors) each, which allows 16 simultaneous slices of data to be collected with each rotation of gantry 12. The scintillator array 56 is coupled to the photodiode array 52 by a thin film of transparent adhesive (not shown).

Switch arrays 80 and 82, FIG. 4, are multi-dimensional semiconductor arrays having similar width as photodiode array 52. In one preferred embodiment, the switch arrays 80 and 82 each include a plurality of field effect transistors (FET). Each FET is electrically connected to a corresponding photodiode 60. The FET array has a number of output leads electrically connected to DAS 32 for transmitting signals via a flexible electrical interface 84. Particularly, about ½ of the photodiode outputs are electrically transmitted to switch array 80 and the other ½ of the photodiode outputs are electrically transmitted to switch array 82. Each detector 20 is secured to a detector frame 77, FIG. 3, by mounting brackets 79.

Switch arrays 80 and 82 further include a decoder (not shown) that controls, enables, disables, or combines photodiode output in accordance with a desired number of slices and slice resolutions. In one embodiment defined as a 16 slice mode, decoder instructs switch arrays 80 and 82 so that all rows of the photodiode array 52 are activated, resulting in 16 simultaneous slices of data available for processing by DAS 32. Of course, many other slice combinations are possible. For example, decoder may also enable other slice modes, including one, two, and four-slice modes.

Figure 5:
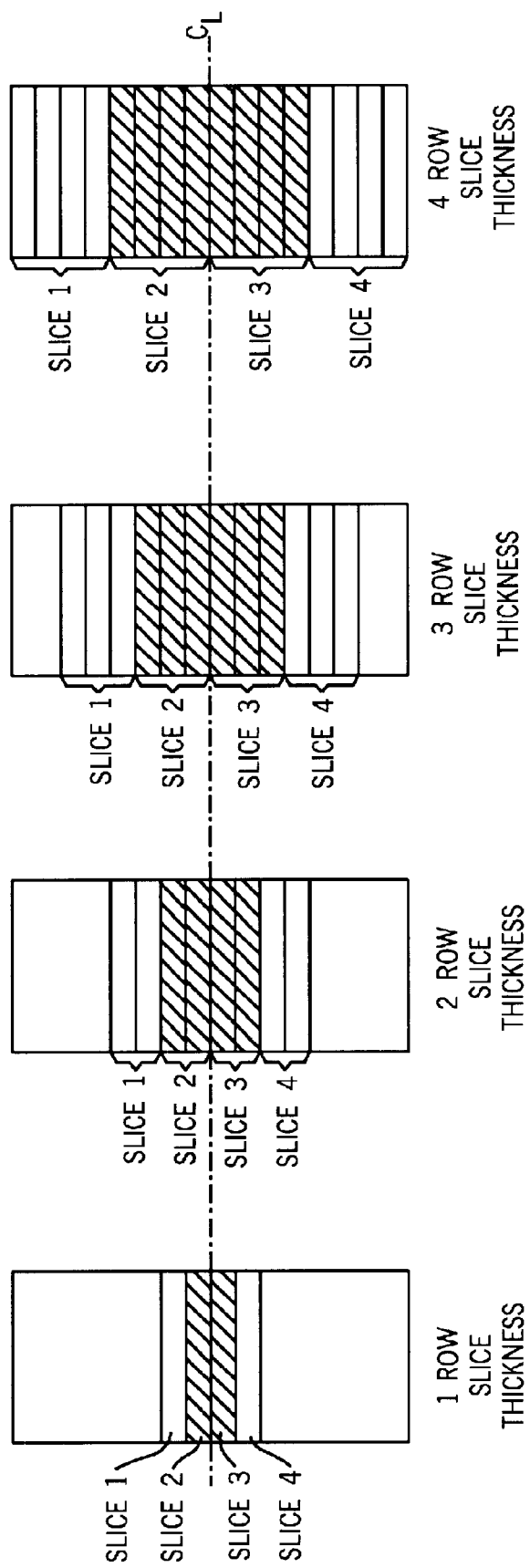
FIG. 5 is illustrative of various configurations of the detector in FIG. 4 in a four-slice mode.

Shown in FIG. 5, by transmitting the appropriate decoder instructions, switch arrays 80 and 82 can be configured in the four-slice mode so that the data is collected from four slices of one or more rows of photodiode array 52. Depending upon the specific configuration-of switch arrays 80 and 82 as defined by the decoder, various combinations of photodiodes 60 of the photodiode array 52 can be enabled, disabled, or combined so that the slice thickness may consist of one, two, three, or four rows of photodiode array elements 60. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 6:
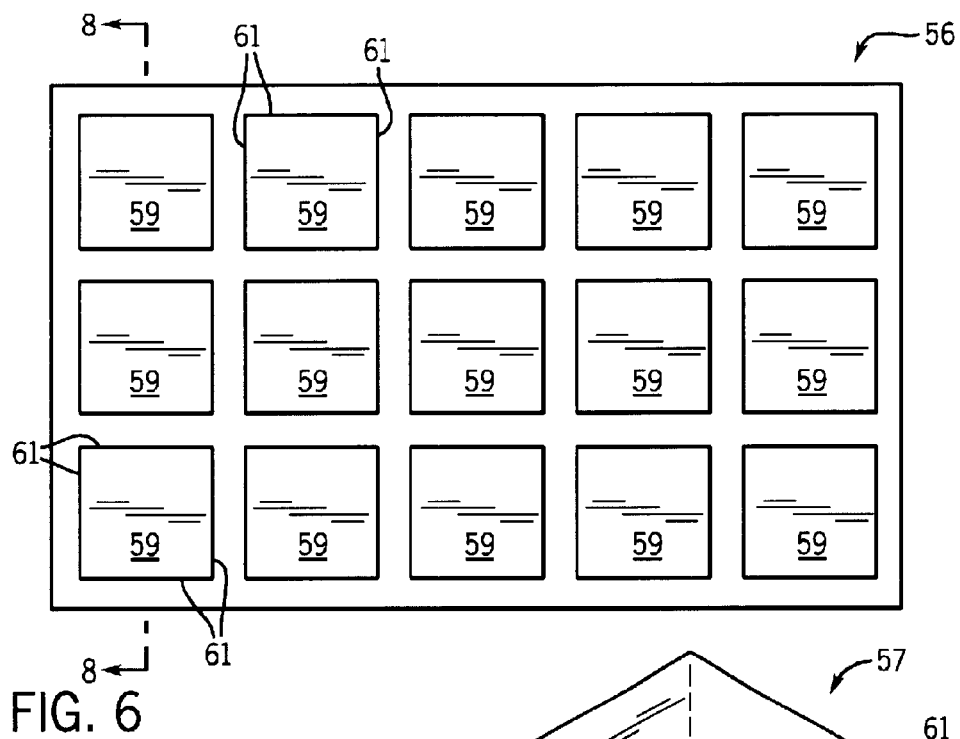
FIG. 6 is a top view of a portion of the detector array shown in FIG. 4.
Figure 7:
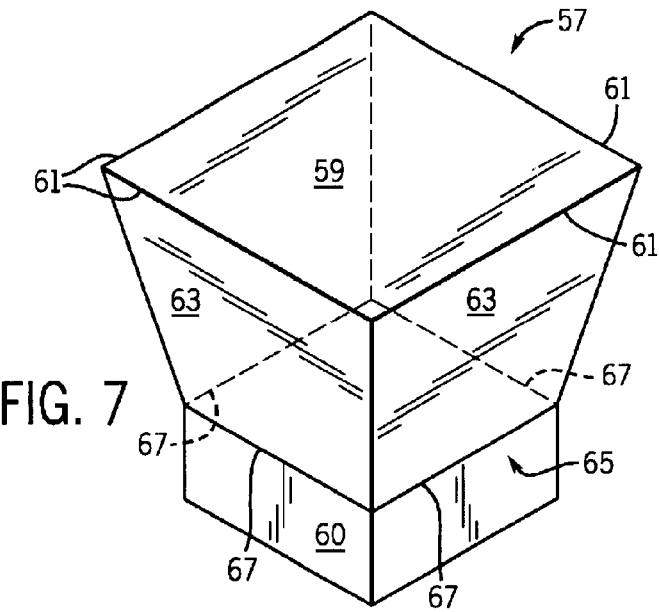
FIG. 7 is a perspective view of a tapered scintillator of the scintillator array shown in FIG. 6.

Now referring to FIG. 6 and 7, scintillator array 56 includes a plurality of tapered scintillators 57. In a preferred embodiment, the number of scintillators 57 is equal to the number of photodiodes 60 of the photodiode array 52. Each scintillator 57 of the scintillator array 56 has an inlet surface 59 configured to receive high frequency electromagnetic energy, such as x-rays. The inlet surface 59 is defined by a plurality of edges 61. In a preferred embodiment, the scintillator inlet 59 has four edges 61, but one of ordinary skill in the art would appreciate that alternate edge configurations, such as triangular, rectangular, and polygonal, are applicable with the present invention. Extending directionally from each inlet edge 61 is a wall 63. Each wall 63 extends to an outlet surface 65. The outlet surface 65, defined by a plurality of exiting edges (not shown), is configured to discharge light energy to the photodiode 60 optically coupled thereto. The plurality of walls 63 extending directionally to the outlet surface 65 focus and converge light energy to the photodiode 60.

Figure 8:
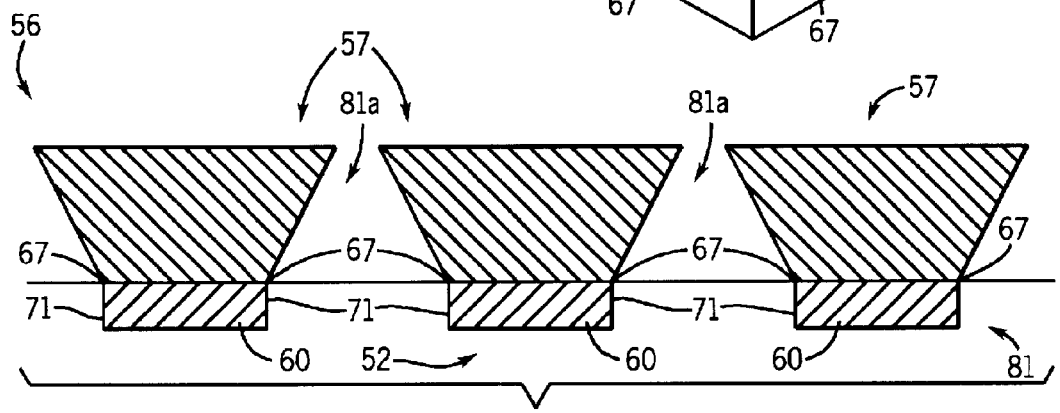
FIG. 8 is a cross-sectional view of the detector taken along line 8—8 of FIG. 6.

Referring to FIG. 8, the photodiode 60, configured adjacent to the outlet surface 65 of the scintillator 57, detects light and transmits corresponding analog signals to DAS 32, FIG. 2. Each photodiode 60 of the photodiode array 52 has a light receiving surface defined by a number of edges 71 configured adjacent to the edges 67 of the light exiting surface 65 of the scintillator 57. In a preferred embodiment, the scintillator array 56 and the photodiode array 52 are of equal dimension, therefore, implementation of a tapered scintillator 57 allows for a photodiode array 52 with more unused or inactive surface area. The increased unused area 81a on the silicon chip 81 between each photodiode 60 allows for routing of an increased number of electrical interconnects, (not shown) forming a signal path. The increase in the number of interconnects yields a higher signal path density and increases the overall electrical performance of the CT system 10.

Accordingly, a method of multi-slice imaging for a computed tomography system is also disclosed. The method includes the steps of emitting high frequency energy, such as x-rays, toward a tapered scintillator array 56 formed by a plurality of tapered scintillators 57. The tapered scintillators 57 convert the high frequency energy to light energy and converge the light energy to a photodiode array 52 formed by a plurality of photodiodes 60. The method also includes fabricating the tapered scintillator array 56 such that each scintillator 57 has an inlet surface 59 defined by a plurality of inlet edges 61, an outlet surface 65 defined by a plurality of the light exiting edges 67, and a plurality of walls 63 extending convergently from the plurality of inlet edges 61 to the plurality of outlet edges 67.

The instant application contemplates several techniques to fabricate a tapered scintillator as described above. In one preferred embodiment, scintillator bulk is immersed in a chemical etchant. After the bulk undergoes immersion for a specific time, the bulk is transferred to a rinse station that assists in removing acid located on the scintillator bulk surface. Once the acid is removed, the scintillator bulk is rinsed and dried. The chemical etchant facilitates anisotropic etching of unprotected portions of the silicon chip 81 which aides in the formation of the tapered scintillator 57.

In another preferred embodiment, plasma is applied to the scintillator bulk to facilitate the forming of a tapered scintillator 57. To form the tapered scintillator 57, the scintillator bulk is loaded into a chamber wherein pressure is reduced by a vacuum system. After the vacuum is established, the chamber is filled with a reactive gas and a frequency field is created through electrodes in the chamber with the aid of a power supply. The frequency field energizes the gas mixture to a plasma state. In the energized state, the gas. mixture attacks unprotected portions the scintillator bulk, and converts the bulk into volatile components which are subsequently removed by the vacuum system. When the volatile components are removed, a tapered scintillator array 56 is formed within the scintillator bulk.

In yet another aspect of the present invention, the tapered scintillator array 56 is formed by accelerating ions forming an ion beam to the scintillator bulk. The scintillator bulk is placed in a vacuum chamber wherein a stream of gas is introduced. When the gas, typically a noble gas, such as argon, enters the chamber, a stream of high energy electrons from a set of cathode and electrodes ionize the atoms of the gas to a high energy state having a positive charge. The scintillator bulk is held on a negatively grounded holder which attracts the ionized gas atoms. The ionized gas atoms accelerate and collect energy while traveling to the scintillator bulk holder. At the surface of the scintillator bulk, the ionized atoms bombard unprotected portions of the scintillator bulk and blast small amounts from the scintillator bulk surface. At the conclusion of the bombardment step, a tapered scintillator 57 results.

In a further embodiment of the present invention, a cutting laser is directed toward the scintillator bulk. The laser is directed by a guide to cut the scintillator bulk so as to form a plurality of entrance edges 61 and a plurality of walls 63 corresponding thereto. The laser guide further directs the laser to cut the scintillator bulk such that the plurality of walls 63 converge to a plurality of exiting edges 67 configured concentric to the plurality of entrance edges 61.

The present invention has been described in terms of the preferred embodiment, and it is recognized that equivalents, alternatives, and modifications, aside from those expressly stated, are possible and within the scope of the appending claims.

What is claimed is:

1. A scintillator array for a CT system comprising a plurality of tapered scintillators formed from a bulk of scintillating material and wherein each scintillator comprises an entrance surface larger than an exiting surface and a plurality of walls extending directionally from the entrance surface to the exiting surface, the scintillator array formed by one of:

applying etchant to the bulk of scintillating material;

applying a plasma of reactive gas to the bulk of scintillating material;

accelerating a plurality of ions forming an ion beam to the bulk of scintillating material; and subjecting the bulk of scintillating material to a cutting laser.

2. The scintillator array of claim 1 further comprising a plurality of signal runs and having a signal run density greater than a signal run density of a scintillator array of non-tapered scintillators.

3. The scintillator array of claim 1 incorporated in a detector array of a CT system, the detector array comprising a photodiode array optically coupled to the scintillator array.

4. A method of manufacturing 2D monolithic scintillator arrays having tapered scintillators, the method comprising the steps of:

fashioning a bulk of scintillator material;

positioning the bulk in a vacuum chamber;

introducing a stream of gas into the vacuum chamber;

ionizing the stream of gas; and directing the ionized stream of gas to a surface the bulk to remove portions of the surface of the bulk.

5. The method of claim 4 wherein the step of positioning the bulk further comprises the step of positioning the bulk on a negatively grounded holder within the vacuum chamber.

6. The method of claim 5 wherein the step of ionizing includes the step of introducing a stream of high energy electrons from a set of cathodes and electrodes to ionize atoms of the stream of gas to a high energy state having a position charge.

7. The method of claim 6 further comprising the step of directing the ionized atoms to the negatively grounded holder.

8. The method of claim 4 further comprising the step of removing unprotected portions of the bulk to construct a tapered scintillator.

9. A method of fabricating a tapered scintillator for use with a CT imaging system, the method comprising the steps of:

depositing scintillator bulk in a chamber;

creating a vacuum in the chamber;

filling the chamber with a reactive gas;

energizing the reactive gas to a plasma state;

converting unprotected portions of the scintillator bulk to volatile components; and removing the volatile components from the scintillator bulk.

10. The method of claim 9 wherein the step of energizing further comprises creating a frequency field within the chamber.

11. The method of claim 9 further comprising the step of protecting portions of the scintillator bulk to isolate the portions from the reactive gas.

12. The method of claim 11 further comprising the step of protecting the portions of the scintillator bulk such that removal of the volatile components yields a tapered scintillator.

13. A method of manufacturing a scintillator array having a plurality of tapered scintillators, the method comprising the steps of:

fashioning a bulk of scintillator material;

immersing the bulk of scintillator material in a chamber of chemical etchant for a predetermined period of time;

upon expiration of the predetermined period of time, removing the bulk of scintillator material from the chamber;

removing chemical etchant from the bulk of scintillator material; and drying the bulk of scintillator material.

14. The method of claim 13 wherein the step of removing chemical etchant comprises the step of rinsing the bulk of scintillator material.

15. The method of claim 13 further comprising the step of protecting portions of the bulk of scintillator material against chemical etchant prior to the step of immersing.

* * * * *